United States Patent
Risi et al.

(10) Patent No.: US 10,550,133 B2
(45) Date of Patent: Feb. 4, 2020

(54) COMPOUNDS, COMPOSITIONS AND METHODS FOR THE TREATMENT OF WOOD

(71) Applicant: PROLAM, SOCIETE EN COMMANDITE, Cap St-Ignace (CA)

(72) Inventors: Benoit Risi, Cap St-Ignace (CA); Eric Levesque, Montreal (CA)

(73) Assignee: PROLAM, SOCIETE EN COMMANDITE, Cap St-Ignace (CA)

( * ) Notice: Subject to any disclaimer, the term of this patent is extended or adjusted under 35 U.S.C. 154(b) by 0 days.

(21) Appl. No.: 16/229,170

(22) Filed: Dec. 21, 2018

(65) Prior Publication Data

US 2019/0194231 A1 Jun. 27, 2019

Related U.S. Application Data

(60) Provisional application No. 62/609,764, filed on Dec. 22, 2017.

(51) Int. Cl.
| | |
|---|---|
| *C07F 5/05* | (2006.01) |
| *B27K 3/34* | (2006.01) |
| *B27K 3/36* | (2006.01) |
| *B27K 3/50* | (2006.01) |

(52) U.S. Cl.
CPC .............. *C07F 5/05* (2013.01); *B27K 3/343* (2013.01); *B27K 3/36* (2013.01); *B27K 2240/70* (2013.01)

(58) Field of Classification Search
CPC .. C07F 5/05; B27K 3/343; B27K 3/36; B27K 2240/70; B27K 3/50; B27K 2240/20
See application file for complete search history.

(56) References Cited

U.S. PATENT DOCUMENTS

| | | | |
|---|---|---|---|
| 1,556,570 A | 10/1925 | Coolidge | |
| 3,083,225 A | 3/1963 | May | |
| 3,410,913 A * | 11/1968 | McMahon, Jr. | ........ C07C 29/52 558/287 |
| 3,674,853 A | 7/1972 | Obenland et al. | |
| 4,076,871 A | 2/1978 | Short et al. | |
| 6,566,014 B1 * | 5/2003 | Fujinami | ................... C07F 5/05 429/307 |
| 2005/0013939 A1 | 1/2005 | Vinden et al. | |
| 2009/0069271 A1 | 3/2009 | Stanimiroff | |
| 2012/0171504 A1 | 7/2012 | Murray | |
| 2013/0267479 A1 | 10/2013 | Jamois | |

FOREIGN PATENT DOCUMENTS

RU 2565201 C2 4/2014

OTHER PUBLICATIONS

Database Registry Chemical Abstracts Service, Columbus Ohio, Accession No. RN 67859-60-3; Entered STN Nov. 16, 1984; p. 1.*
Aubrey, D. W., "373. Cyclic organic boron compounds. Part V. Infrared spectra of borazoles and boroxoles." Journal of the Chemical Society (Resumed) (1961): 1931-1938.*
Morgan, A. B., "Synthesis, flame-retardancy testing, and preliminary mechanism studies of nonhalogenated aromatic boronic acids: A new class of condensed-phase polymer flame-retardant additives for acrylonitrile-butadiene-styrene and polycarbonate." Journal of Applied Polymer Science 2000 76(8):1257-1268.*

* cited by examiner

*Primary Examiner* — John M Mauro
(74) *Attorney, Agent, or Firm* — Wood, Phillips, Katz, Clark & Mortimer

(57) ABSTRACT

Here are described boroxine-containing compounds and their compositions for the treatment of wood. For instance, the treatment of wood includes its protection against moisture and/or degradation caused by insects or microbes.

32 Claims, No Drawings

COMPOUNDS, COMPOSITIONS AND METHODS FOR THE TREATMENT OF WOOD

RELATED APPLICATION

This application claims priority to U.S. provisional application No. 62/609,764 filed on Dec. 22, 2017, the content of which is incorporated herein by reference in its entirety for all purposes.

TECHNICAL FIELD

The technical field generally relates to compounds and compositions for use in the treatment of wood, especially for protection of wood against moisture, insects and microbes including fungi and molds.

BACKGROUND

Wood has always been and still is an important material for indoor or outdoor construction as well as in furniture, railway ties and utility poles. However, since wood is a cellulosic material, and therefore organic in nature, it is susceptible to degradation and decay when exposed to humidity and biological attacks from insects, mold, etc. Thus, protection against deterioration is necessary and has been accomplished in the past using various methods.

One of the commonly known methods for protecting wood includes impregnation of wood pieces with oil-borne preservatives such as creosote or a creosote-containing composition. These are generally found to be toxic, especially for workers involved in wood treatment and/or installation of treated wood pieces. This toxicity also prevents these treated wood pieces to be used in settings outside of railway ties, utility poles, etc. Creosote lixiviation in nature over time also results in environmentally detrimental effects. Furthermore, while creosote-based preservatives' effect may last up to thirty years in a cold northern climate, these preservatives will lose efficiency much more rapidly in warmer climates. Other known wood treatments include water-borne preservatives such as arsenic salts, boric acid, chromium salts, and others. Water-borne preservatives are generally known to be more prone to water induced lixiviation, which results in the preservatives' active agents leaching into the environment, some of these active agents being highly toxic. The lixiviation of the preservatives from a treated wood piece also means rapid loss of protection.

Accordingly, there is a need for alternative compounds and compositions for protecting wood surfaces and fibers from degradation and decay. For instance, these compounds and compositions may have improved properties in comparison to known wood preservatives, such as reduced water solubility, reduced or prevented lixiviation of the active product, improved efficacy or retention of efficacy over time, reduced toxicity, and/or less or nearly absent environmental negative impact.

SUMMARY

According to one aspect, the present technology relates to boroxine compounds, dimers and oligomers which may be used for the treatment of wood. For instance, such a compound is of Formula I:

wherein,

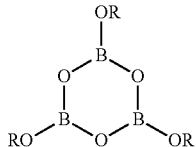

Formula I

R is, independently in each instance, A or a primary or secondary, linear or branched $C_{8-20}$alkyl group; and A is a primary, secondary, or tertiary, linear or branched $C_{2-10}$alkylene group derived from a glycol (e.g. 1,2-diol or a 1,3-diol), wherein said alkylene group links at least two compounds of Formula I.

In one embodiment, R is, independently in each instance, selected from primary or secondary, linear or branched $C_{8-20}$alkyl groups. In another embodiment, at least one R is A. In one embodiment, one R is A and the compound of Formula I is a dimer.

In another embodiment, the compound is of Formula II:

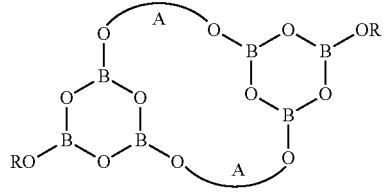

Formula II wherein,

A is, independently in each instance, selected from primary, secondary, or tertiary, linear or branched $C_{2-10}$alkylene group derived from a 1,2-diol or a 1,3-diol; and R is as defined above.

In a further embodiment, the compound is of Formula III:

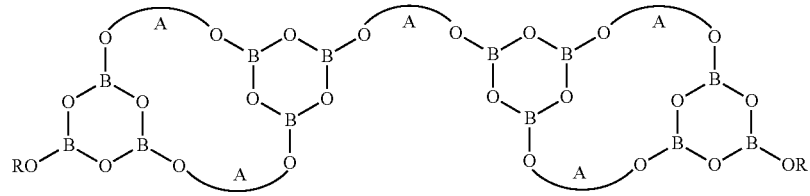

Formula III wherein A and R are as defined above

In another embodiment, the compound is of Formula I, II or III and at least one R is selected from 2-octyl, ethylhexyl, dodecyl, and octadecyl.

In a further embodiment, the compound is of Formula IV:

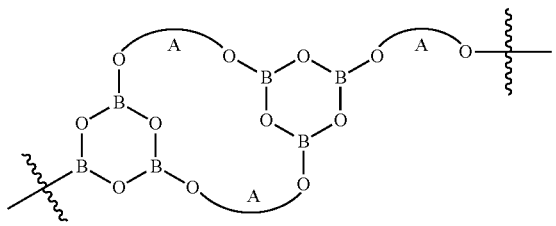

Formula IV wherein A is, independently in each instance, as defined above and wherein the waves each represent a bound between multiple units of Formula IV in a polymer or oligomer form.

In one embodiment, the compound is of Formula II, III, or IV and at least one A is selected from 1,2-propylene, 1,3-propylene, and 2-methyl-2,4-pentylene.

In a further embodiment, the compound is selected from Compounds A1, A2, B1 to B4, C1 to C3, and D1 to D3 as defined herein, or an isomer thereof.

According to another aspect, the present technology relates to compositions comprising at least one compound of Formula I, II, III or IV as defined herein. In one example, the composition comprises at least two compounds of Formula I, II, III or IV. In another example, the composition comprises at least one compound of Formula I, II, III or IV together with a diluent. In one embodiment, the diluent comprises a paraffin wax, an ester wax of vegetal or animal origin (e.g. beeswax, carnauba wax), a fatty ester (e.g. vegetable or animal oils and greases, biodiesel), tar, a petrochemical oil, petroleum naphtha, petroleum ether, a volatile ester (e.g. ethyl acetate, isopropyl acetate), and/or a volatile ether (e.g. diethyl ether, MTBE). For instance, the diluent may comprise a paraffin wax.

According to a further aspect, also described is a treated wood item, where a surface of the wooden item comprises at least one compound or composition as herein defined.

According to a further aspect, this technology relates to a compound or composition as defined herein, for use in the treatment of wood. Accordingly, the use of a compound or composition as defined herein, for the treatment of wood is also contemplated. For instance, the treatment comprises wood protection against moisture, and/or the treatment comprises prevention or reduction of degradation caused by insects, microbes (e.g. fungi), or a combination thereof.

According to yet another aspect, the present technology further relates to a method for protecting wood, said method comprising a step of applying a compound or a composition as herein defined, on a wood surface. For instance, the step of applying comprises impregnating the wood with the compound or composition. In one example, the compound or composition may be melted before application and/or impregnation. In one embodiment, the protection comprises protecting the wood against moisture, or preventing or reducing degradation caused by insects, microbes (e.g. fungi), or a combination thereof.

DETAILED DESCRIPTION

The following detailed description and examples are illustrative and should not be interpreted as further limiting the scope of the invention.

All technical and scientific terms and expressions used herein have the same definitions as those commonly understood by the person skilled in the art relating to the present technology. The definition of some terms and expressions used is nevertheless provided below.

The chemical structures described herein, are drawn according to conventional standards. Also, when an atom, such as a carbon atom, as drawn seems to include an incomplete valency, then the valency is assumed to be satisfied by one or more hydrogen atoms even though these are not necessarily explicitly drawn.

As used herein, the term "alkyl" refers to saturated hydrocarbons including linear or branched alkyl groups. Examples of alkyl groups include, without limitation, methyl, ethyl, propyl, butyl, pentyl, hexyl, heptyl, octyl, nonyl, decyl, undecyl, dodecyl, pentadecyl, hexadecyl, octadecyl, isopropyl, tert-butyl, sec-butyl, isobutyl, isoamyl, neopentyl, and the like. When an alkyl group is located between two functional groups, then the term "alkyl" also encompasses alkylene groups such as methylene, ethylene, propylene, and the like. The term "$C_m$-$C_n$alkyl" refers to an alkyl group having from the indicated "m" number of carbon atoms to the indicated "n" number of carbon atoms.

The term "alkylene" refers to an alkyl group located between two functional groups. Examples of alkylene groups include, without limitation, 1,2-ethylene, 1,2-propylene, 1,3-propylene, 1,3-butylene, and their analogs further substituted with alkyl groups such as methyl and ethyl (e.g. derived from neopentylene glycol, hexylene, i.e. 2-methyl-2,4-pentylene). The term "$C_m$-$C_n$alkylene" refers to an alkylene group having from the indicated "m" number of carbon atoms to the indicated "n" number of carbon atoms including alkyl substituents if present.

The term "isomer" or an equivalent refers to enantiomers, diastereomers, constitutional isomers, position isomers or structural isomers.

The present technology relates to trialkoxyboroxines, also called trialkylmetaborates or 2,4,6-trialkoxy-1,3,5,2,4,6-trioxatriborinanes, collectively referred to herein as boroxines or simply as "compounds". The compounds may be in pure form or as a mixture of two or more compounds, including a single boroxine ring, or two (dimers) or more (oligomers) boroxine rings. As will be further described below, the present compounds may be prepared by reacting a boron source such as boric acid, a fatty alcohol (e.g. having at least 8 carbon atoms), for instance, in the presence of a diol (e.g. a 1,2- or 1,3-diol). For example, the compounds comprise boron within the cyclic structure, this element having biocidal properties. Hydrophobic alkyl groups are included to increase the product's resistance to hydrolysis and lixiviation. Alkylene chains linking muliple boroxine cyclic structures may be further inserted, allowing to reduce the content in hydrophobic alkyl groups, thereby increasing the boron content. When hydrophobic alkyl groups are not included in the structure and only alkylene chains are present, the resulting product is mainly comprised of polymers and oligomers of boroxine cyclic structures.

As such, the compounds as herein defined comprise at least one compound selected from Formula I, II, III or IV:

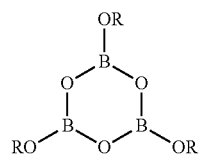

Formula I

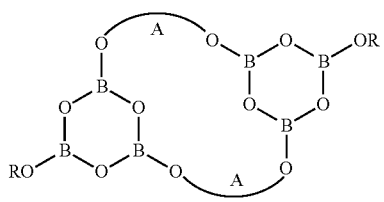

Formula II

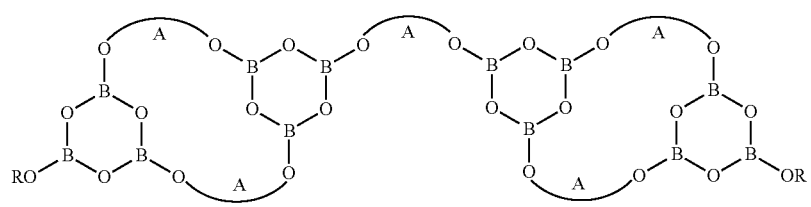

Formula III

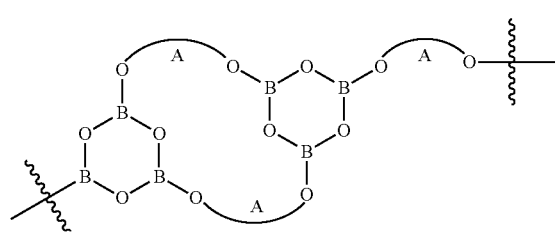

Formula IV wherein,

R is, independently in each instance, a group A or a primary or secondary, linear or branched $C_{8-20}$alkyl group; and A is a primary, secondary, or tertiary, linear or branched $C_{2-10}$alkylene group derived from a glycol (1,2-diol or a 1,3-diol), wherein said alkylene group links at least two compounds of Formula I.

In Formula IV, A is, independently in each instance, as defined above and the waves each represent a bound between multiple units of Formula IV in a polymer form.

In one example, the compound is of Formula I and R is, independently in each instance, selected from primary or secondary, linear or branched $C_{8-20}$alkyl groups. In another example, the compound is of Formula I and at least one R is A. In a further example, R is selected from 2-octyl, ethylhexyl, dodecyl, and octadecyl in any one of Formula I, II or III. In another example, the compound is of Formula II, III, or IV and at least one A is selected from 1,2-propylene, 1,3-propylene, and 1,3,3-trimethylpropylene. In another example, the compound is of Formula I, II or III and R is the same in each instance. In another example, the compound is of Formula II, III or IV and A is the same in each instance.

Examples of compounds of Formula I include Compounds A1 and A2:

Compound A1

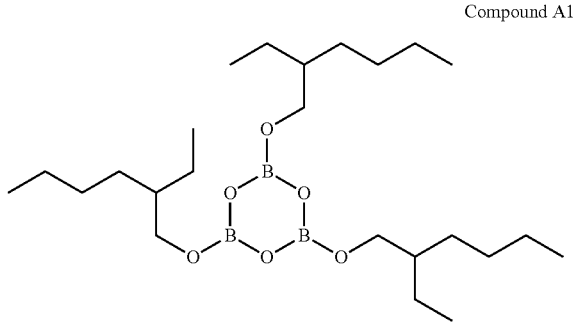

Compound A2

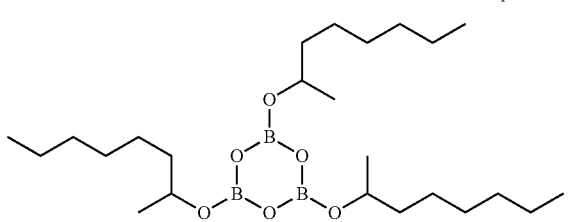

Examples of compounds of Formula I or II include Compounds B1 to B4:
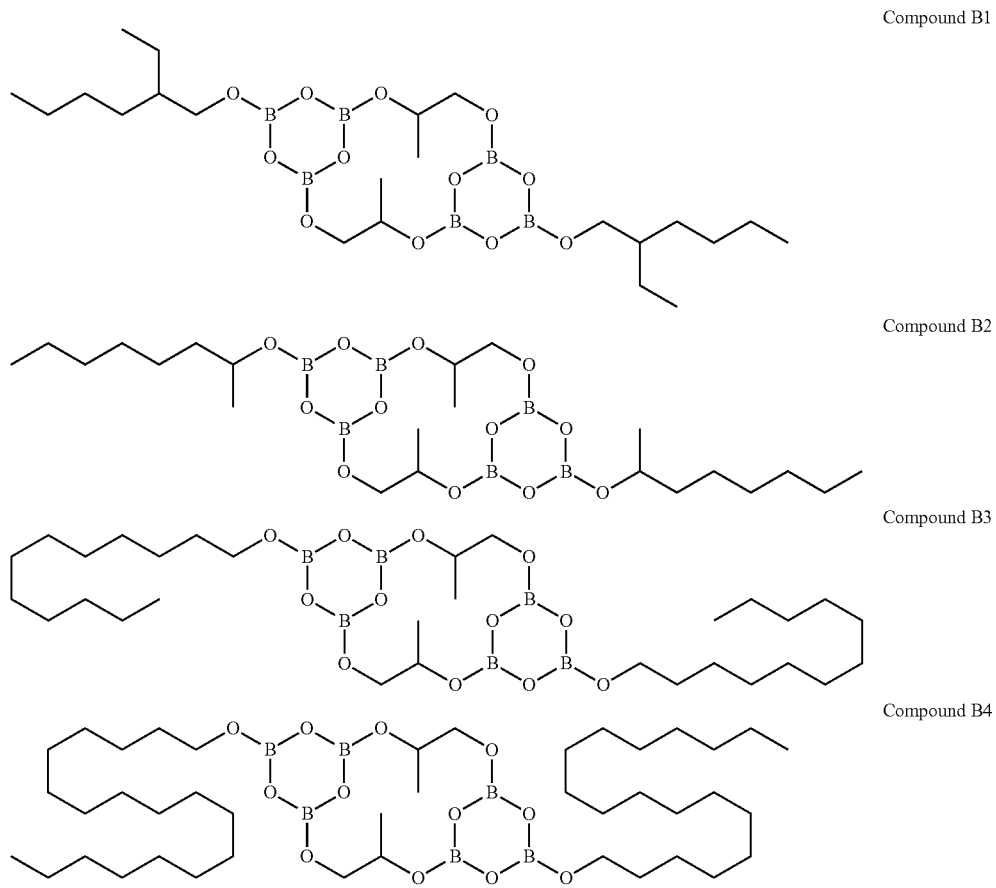
or an isomer thereof.
Examples of compounds of Formula I or III include Compounds C1 to C3:
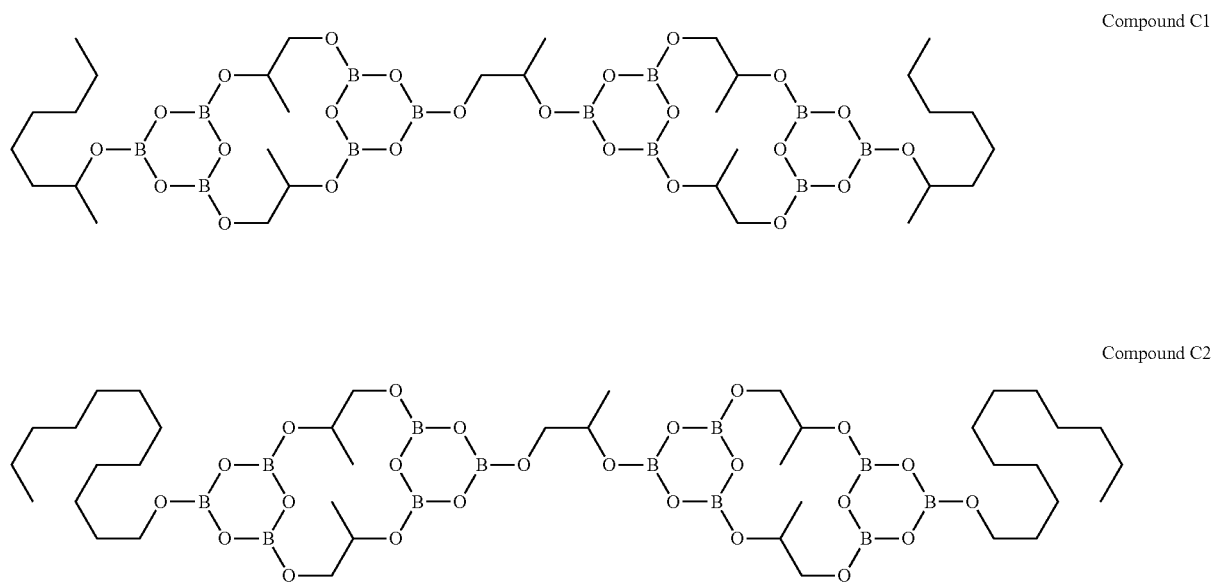

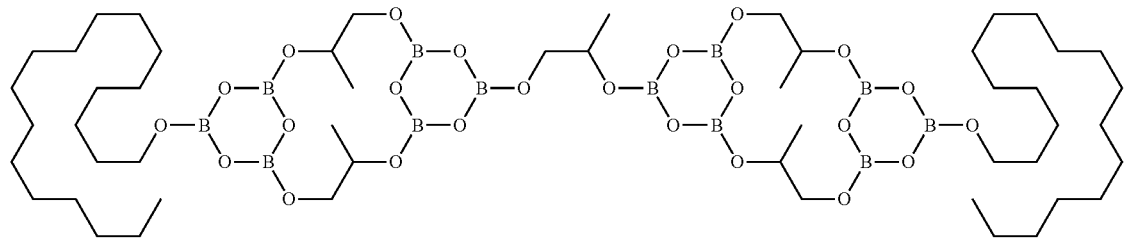

Compound C3 or an isomer thereof.

Examples of compounds of Formula I or IV include Compounds D1 to D3:

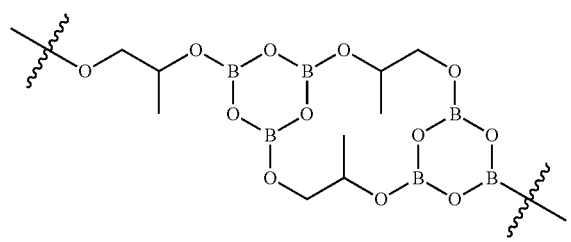

Compound D1

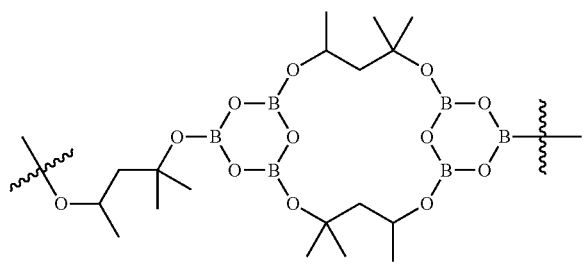

Compound D2

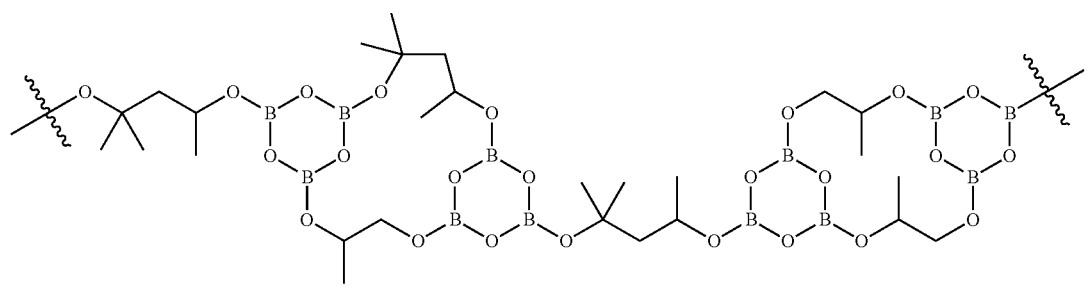

Compound D3 or an isomer thereof.

A process for the preparation of boroxines as defined herein comprises reacting an alcohol, a diol, or an alcohol and a diol in the required stoichiometric amounts with a boron source, e.g. boric acid or a boron oxide such as $B_2O_3$, while removing generated water. In one example, water removal is achieved by heating under stirring at a temperature of 100° C. or above (e.g. around 110° C.), while using a water trap such as a Dean-Stark apparatus. In one example, the heating temperature is kept below 200° C., or below 190° C., or below 180° C. The reaction may be carried out without the addition of an additional solvent. For instance, the process comprises reacting boric acid with a diol, an alcohol or both, in an amount corresponding to a ratio of 1 mole of boric acid for 1 mole of OH group present on the alcohol or diol molecule.

For example, a compound of Formula I wherein R is an alkyl group is prepared by reacting an alcohol and boric acid in a molar ratio of about 1:1. A compound of Formula I, wherein one R is A, may also be prepared by using a boric acid:alcohol:diol molar ratio of about 6:4:1. A compound of Formula II may be prepared by using a boric acid:alcohol:diol molar ratio of about 3:1:1. The same molar ratio may also result in a compound of Formula I, comprising one unit of Formula II, wherein one R is A attached to a boroxine of Formula II featuring two alkyl groups. A compound of Formula III may be obtained by reacting together the three above elements in a boric acid:alcohol:diol molar ratio of about 12:2:5. Finally, polymers of Formula IV may be obtained by reacting a diol and boric acid according to the above process in a boric acid:diol molar ratio of about 2:1. The resulting product may also be a mixture or the various compounds, or of one or more main compounds and other minor by-products.

Also contemplated are products prepared by a process as defined herein, the product being a pure or substantially pure compound or a mixture of compounds of Formula I. For example, a compound which is prepared by reacting an alcohol and boric acid in a molar ratio of about 1:1; by reacting boric acid, an alcohol and a diol in a boric acid: alcohol:diol molar ratio of about 6:4:1, of about 3:1:1, or of about 12:2:5. Finally, oligomers or polymers and mixtures comprising them are prepared by reacting a diol and boric acid according to the above process in a boric acid:diol molar ratio of about 2:1.

For example, contemplated is a compound or mixture of compounds prepared by reacting two or more diols and/or two or more alcohols in the required stoichiometric amounts with a boron source, e.g. boric acid or a boron oxide such as $B_2O_3$, while removing generated water. For instance, the preparation comprises reacting boronic acid, hexylene glycol and 1,2-propylene glycol in a molar ratio of about 4:1:1. (i.e. 2: ½: ½).

Compositions comprising at least one compound as defined herein are also herein contemplated. As previously mentioned, the present compounds may be present as a mixture of at least two compounds as defined herein, thereby forming a composition. Alternatively, the composition may also comprise at least one compound as defined herein together with a diluent. For instance, the diluent may comprise one or more of a paraffin wax, an ester wax of vegetal or animal origin (e.g. beeswax, carnauba wax, etc.), a fatty ester (e.g. vegetable or animal oils or greases, biodiesel), tar, a petrochemical oil, petroleum naphtha, petroleum ether, a volatile ester (e.g. ethyl acetate, isopropyl acetate, etc.), a volatile ether (diethyl ether, MTBE, etc.), and the like.

The present compound or mixture of compounds may be applied as is, for instance, by heating the compound or mixture at or above its melting temperature to form a liquid composition which may be applied on a wood surface. Any method of application, including spraying, spreading in any form, pressure penetration, or immersing in the melted compound or mixture is contemplated. Similarly, if the compound or mixture is in the form of a composition comprising a diluent, such a composition may be applied in liquid form (at room temperature if liquid or after preheating for melting the composition) using any known methods such as those defined above. One will understand that a reference to application on wood may further include impregnation of the piece of wood being treated, i.e. penetration of the compound or composition into the wood fibers.

For instance, the application of the compounds or compositions serves as a protecting barrier. Because of its hydrophobic nature, lixiviation of the compounds or compositions from the wood surfaces or fibers may be prevented or reduced while being less toxic and/or having a lesser negative impact for the environment in comparison to other current commercial treatments.

Such a hydrophobic boron-containing barrier may have a protecting effect on wood surfaces and potentially into the wood fibers, such protecting effect including protection against moisture and degradation and decay caused by insects and/or microbes (e.g. bacteria, fungi or molds).

The wooden item being treated may be for indoor and/or outdoor use, for example, indoor and outdoor construction material (e.g. including structure, floors, walls, patios etc.), furniture, railroad ties, power line utility poles, or any wood piece which may be susceptible to degradation and/or may benefit from protection as defined herein. Any type of woods, including softwoods and hardwoods, may be treated using the present method, compounds and compositions, depending on intended purpose.

EXAMPLES

The following non-limiting examples are illustrative embodiments and should not be construed as further limiting the scope of the present invention.

Example 1: Synthesis of Boroxines

General Procedure:

A 5-Liter, 3-necked round-bottomed flask is equipped with a mechanical agitator, a Dean-Stark water trap, a thermometer and a heating mantle. Alcohol(s) and/or Diol(s) are added. The water trap is filled with the alcohol (if present). Boric acid is added under strong agitation. The heterogenous mixture is heated to 110° C. (water started collecting in the trap). Heating and agitation continued until water stopped collecting, keeping the liquid temperature below 180° C. The homogenous viscous liquid is cooled to 90° C. and maintained at that temperature for one hour. A white precipitate appears. The precipitate is filtered out while maintaining the temperature at 90° C. The filtrate (desired product) may solidify upon cooling. Reactions are performed to achieve a scale of about 1 kg of product. Reaction conditions for the preparation of each compound as well as the boron content and phase of the obtained product are summarized in Table 1.

TABLE 1

Reaction conditions and results

| Compound | Alcohol[a] | Diol D[b] | Molar ratio (Boric acid: Alcohol:Diol) | Mass % Boron (measured) | Phase at 25° C. |
|---|---|---|---|---|---|
| A1 | eH | — | 1:1:0 | 22% $B_2O_3$ 7% B | Liquid |
| A2 | Oc | — | 1:1:0 | 22% $B_2O_3$ 7% B | Liquid |
| B1 | eH | PG | 3:1:1 | 36% $B_2O_3$ 11% B | Viscous liquid |
| B2 | Oc | PG | 3:1:1 | 34% $B_2O_3$ 11% B | Viscous liquid |
| B3 | Dd | PG | 3:1:1 | 24% $B_2O_3$ 10% B | Viscous liquid |
| B4 | Od | PG | 3:1:1 | 16% $B_2O_3$ 7% B | Solid, Melting point = 55-70° C. |
| C2 | Dd | PG | 12:2:5 | 35% $B_2O_3$ 12% B | Viscous liquid |
| C1 | Oc | PG | 12:2:5 | 38% $B_2O_3$ 12% B | Viscous liquid |
| D1 | — | PG | 2:0:1 | 49% $B_2O_3$ 15% B | Solid/gum Melting point = 90° C. |
| D2 | — | HG | 2:0:1 | 34% $B_2O_3$ 11% B | Solid/gum Melting point = 110° C. |
| D3 | — | 1:1 HG/PG | 2:0:1 | 37% $B_2O_3$ 12% B | Viscous liquid |

[a]Oc: 2-octanol; eH: 2-ethylhexan-1-ol; Dd: dodecanol; Od: n-octadecanol
[b]PG: 1,2-popylene glycol; HG: hexylene glycol (also called 2-methyl-2,4-pentanediol)

Compound A1: The above general procedure is used, with 2-ethylhexanol as the alcohol and no diol. The reaction is carried out at a temperature between 105° C. and 190° C. The product has a melting point below 25° C.

Compound A2: The procedure for preparing Compound A1 is used, except 2-octanol replaces 2-ethylhexanol as the alcohol and also to fill the trap. The reaction is carried out at a temperature between 125° C. and 190° C. The product has a melting point below 25° C.

Compound B1: The above general procedure is used, with 2-ethylhexanol as the alcohol and 1,2-propylene glycol as the diol. The reaction is carried out at a temperature between 105° C. and 170° C. The product is obtained by high temperature (90° C.) filtration. Viscosity reduces rapidly with increasing temperature. The product has a melting point below 25° C.

Compound B2: The procedure for preparing Compound B1 is used, except that the alcohol used is 2-octanol. The reaction is carried out at a temperature between 105° C. and 180° C. The product has a melting point below 25° C.

Compound B3: The procedure for preparing Compound B1 is used, except that the alcohol used is n-dodecanol. The reaction is carried out at a temperature between 105° C. and 200° C. The product has a melting point below 25° C.

Compound B4: The procedure for preparing Compound B1 is used, except that the alcohol used is n-octadecanol. The reaction is carried out at a temperature between 110° C. and 180° C. The product has a melting point of 55° C. to 70° C.

Compound C1: The above general procedure is used, with 2-octadecanol as the alcohol and 1,2-propylene glycol as the diol. The reaction is carried out at a temperature between 110° C. and 180° C. A small amount of the product is isolated for analysis by high temperature filtration (the solid by-product separates from the desired solid starting at 75° C.). The product has a melting point below 25° C.

Compound C2: The procedure for preparing Compound C1 is used, except that the alcohol used is n-dodecanol. The reaction is carried out at a temperature between 110° C. and 180° C. The product has a melting point below 25° C. Viscosity reduces rapidly with increasing temperature. The desired liquid separates well from the liquid starting at 115° C. Once the solid is separated, the temperature may be lowered to 90° C. The product has a melting point below 25° C.

Compound D1: The above general procedure is used, with no alcohol and 1,2-propylene glycol as the diol. The water trap is left empty. The reaction is carried out at a temperature between 110° C. and 145° C. A liquid principally consisting of water is collected in the trap. The reaction is carried out at a temperature between 110° C. and 145° C.). If the vapor temperature exceeds 150° C. or if gas formation suddenly stops, then the reaction is complete. The product is isolated by high temperature filtration at 90° C. The product is a solid at 4° C., a non-Newtonian liquid at 25° C. Malleable like hard modelling clay, grains stick together in the container. On the other hand, they are smashed to pieces under mechanical shocks. The product is a transparent liquid at 90° C. but is still very viscous.

Compound D2: The procedure for preparing Compound D1 is used, except that the diol used is 1,3,3-trimethylpropylene glycol (Hexylene glycol). The reaction is carried out at a temperature between 110° C. and 140° C. If the vapor temperature exceeds 150° C. or if gas formation suddenly stops, then the reaction is complete. High temperature filtration needed to be carried out at 135° C. as mixture was solid at 90° C.

Compound D3: The procedure for preparing Compound D1 is used, except that the diol used is a 1:1 (molar) mixture of 1,2-propylene glycol and 1,3,3-trimethylpropylene glycol (Hexylene glycol). The reaction is carried out at a temperature between 110° C. and 140° C.). If the vapor temperature exceeds 150° C. or if gas formation suddenly stops, then the reaction is complete. The product has a melting point below 25° C.

Example 2: Boron Determination by Hydrolysis and Titration

A known quantity of trialkoxyboroxine sample is dissolved in isobutanol (approximately 100 mL/g). Sorbitol (3 molar equivalents in relation to expected boron) and 1.00 M NaOH standard solution (1.5 molar equivalents in relation to expected boron) are added and mixture is refluxed for one hour. Phenolphthalein (1 mg) is added and the mixture is titrated with 1.00 M HCl standard solution until the mixture turns colorless. The initial number of moles of NaOH minus the number of moles of HCl equals the number of moles of boron present in the sample. Results obtained for the prepared compounds are summarized in Table 1 above.

Example 3: Formulation

The final product can be used as is for wood treatment (e.g. timber) or can be diluted with a suitable additive, solvent or diluent. Examples of additives, solvents or diluents include paraffin wax, ester waxes of vegetal or animal origin (e.g. beeswax, carnauba wax), fatty esters (vegetable or animal oils and greases), tar, petrochemical oils, petroleum naphtha, petroleum ether, volatile esters (e.g. ethyl acetate, isopropyl acetate), volatile ethers (e.g. diethyl ether, MTBE).

Numerous modifications could be made to any of the embodiments described above without departing from the scope of the present invention. Any references, patents or scientific literature documents referred to in the present document are incorporated herein by reference in their entirety for all purposes.

The invention claimed is:
1. A compound of Formula I:

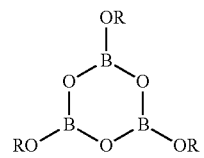

Formula I wherein,

R is, independently in each instance, a group A or a primary or secondary, linear or branched $C_{8-20}$alkyl group; and A is a primary, secondary, or tertiary, linear or branched $C_{2-10}$alkylene group wherein the $C_{2-10}$alkylene group comprises an ethylene or propylene between the oxygen atoms attached thereto, wherein said alkylene group links at least two compounds of Formula I; and wherein at least one R is A.

2. The compound of claim 1, wherein said compound is of Formula II:

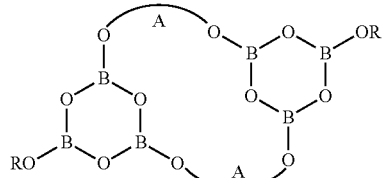

Formula II wherein,

A is, independently in each instance, selected from primary, secondary, or tertiary, linear or branched $C_{2-10}$alkylene group wherein the $C_{2-10}$alkylene group comprises an ethylene or propylene between the oxygen atoms attached thereto; and R is as defined in claim 1.

3. The compound of claim 1, wherein said compound is of Formula III:

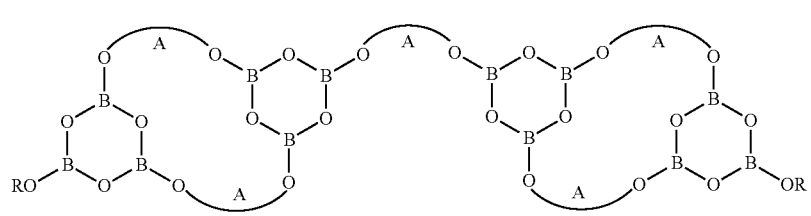

Formula III wherein A and R are as defined in claim 2.

4. The compound of claim 1, wherein at least one R is selected from 2-octyl, ethylhexyl, dodecyl, and octadecyl.

5. The compound of claim 1, wherein said compound is of Formula IV:

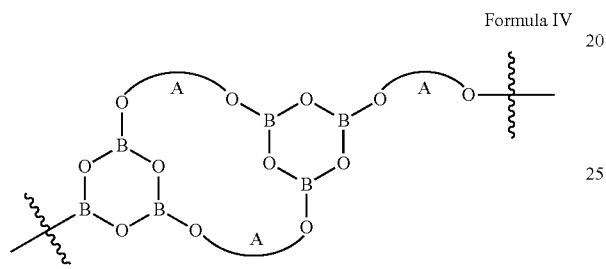

Formula IV wherein A is, independently in each instance, as defined in claim 2, and wherein the waves each represent a bond between multiple units of Formula IV in an oligomer or polymer form.

6. The compound of claim 1, wherein at least one A is selected from 1,2-propylene, 1,3-propylene, and 2-methyl-2,4-pentylene.

7. The compound of claim 1, wherein said compound is selected from:

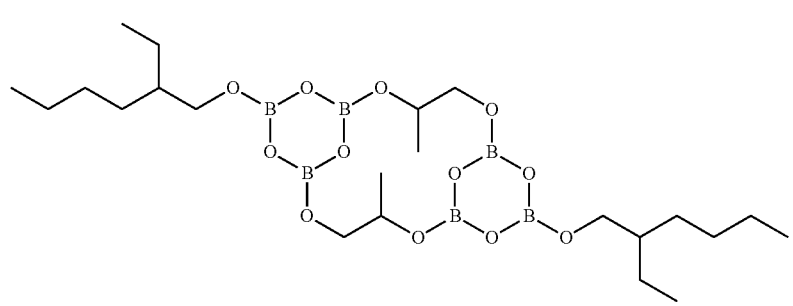

Compound B1

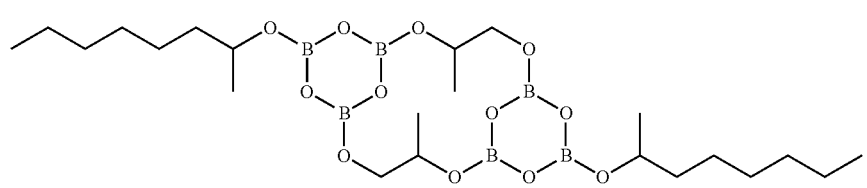

Compound B2

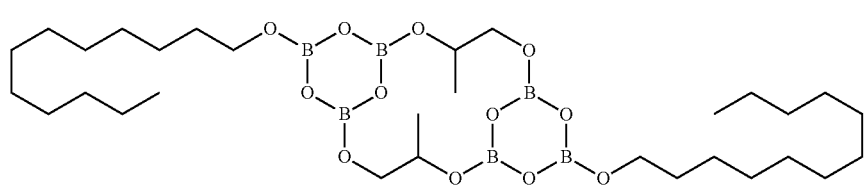

Compound B3

-continued
Compound B4
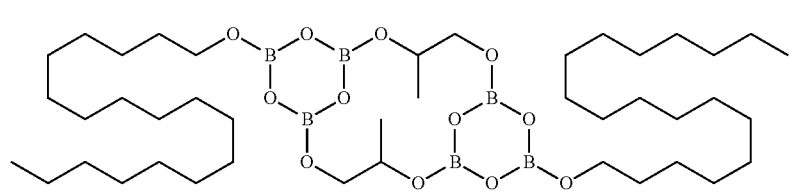
Compound C1
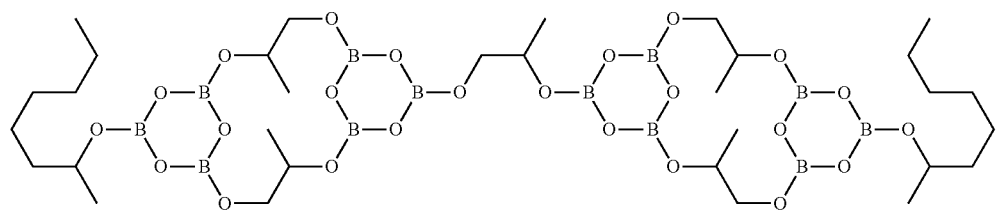
Compound C2
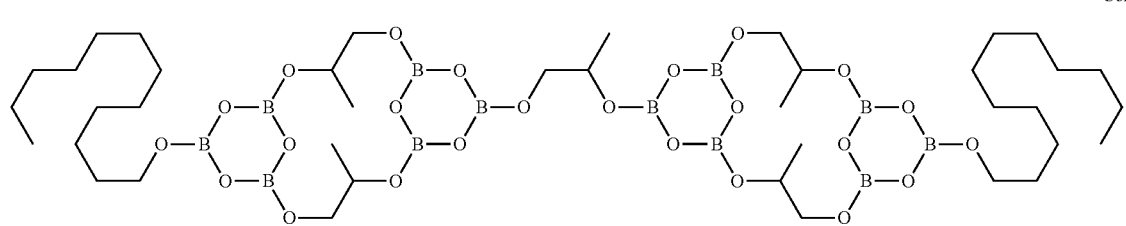
Compound C3
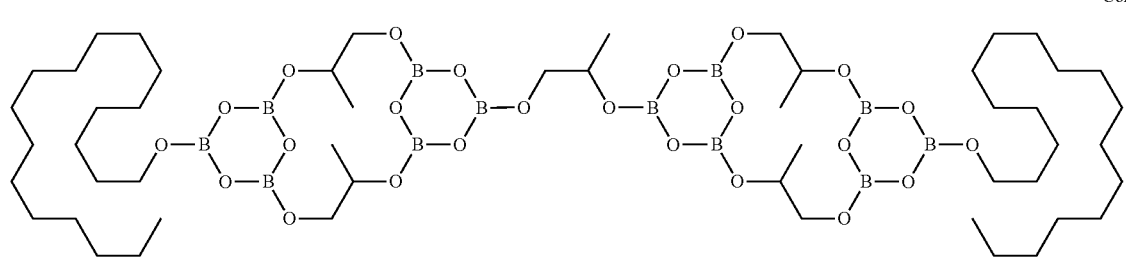
Compound D1
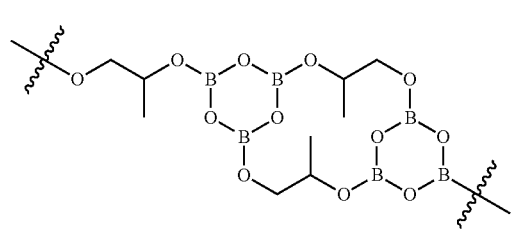
Compound D2
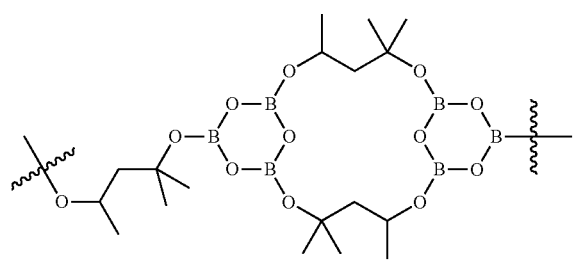
Compound D3
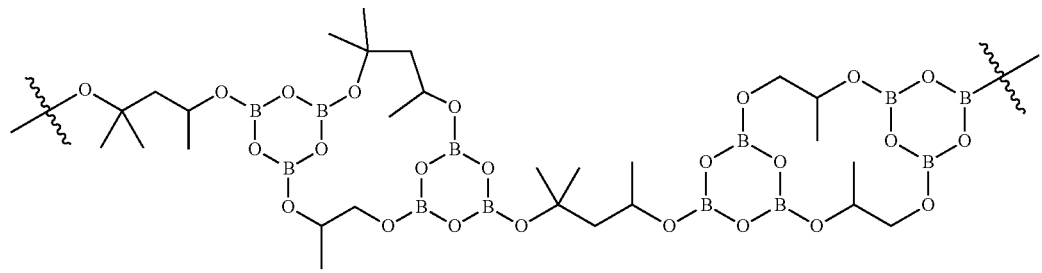

wherein the waves in Compounds D1, D2 and D3, each represent a bond between multiple Compounds D1, D2 and D3 respectively, in an oligomer or polymer form.

8. A composition comprising at least two compounds as defined in claim 1.

9. A composition comprising at least one compound as defined in claim 1 together with a diluent.

10. A treated wooden item, wherein a surface of said wooden item comprises a composition of claim 9.

11. A treated wooden item, wherein a surface of said wooden item comprises at least one compound of Formula I:

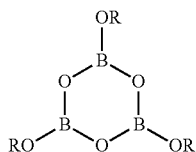

Formula I wherein

R is, independently in each instance, a group A or a primary or secondary, linear or branched $C_{8-20}$alkyl group; and A is a primary, secondary, or tertiary, linear or branched $C_{2-10}$alkylene group wherein the $C_{2-10}$alkylene group comprises an ethylene or propylene between the oxygen atoms attached thereto, wherein said alkylene group links at least two compounds of Formula I.

12. The treated wood item of claim 11, wherein said compound is of Formula II:

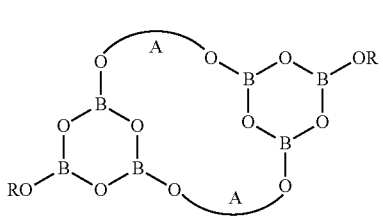

Formula II wherein,

A is, independently in each instance, selected from primary, secondary, or tertiary, linear or branched $C_{2-10}$alkylene group wherein the $C_{2-10}$alkylene group comprises an ethylene or propylene between the oxygen atoms attached thereto; and R is as defined in claim 11.

13. The treated wood item of claim 11, wherein said compound is of Formula III:

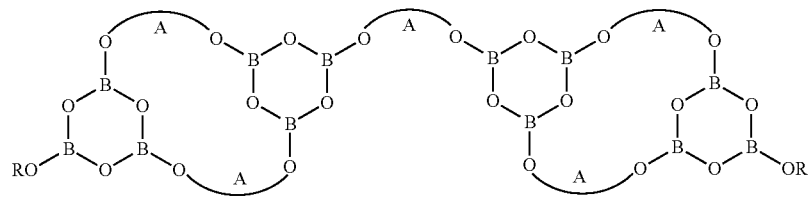

Formula III wherein A and R are as defined in claim 12.

14. The treated wood item of claim 11, wherein said compound is of Formula IV:

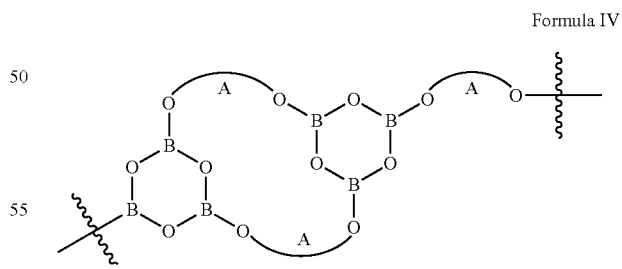

Formula IV wherein A is, independently in each instance, as defined in claim 12, and wherein the waves each represent a bond between multiple units of Formula IV in an oligomer or polymer form.

15. The treated wood item of claim 11, wherein said compound is selected from:

Compound A1
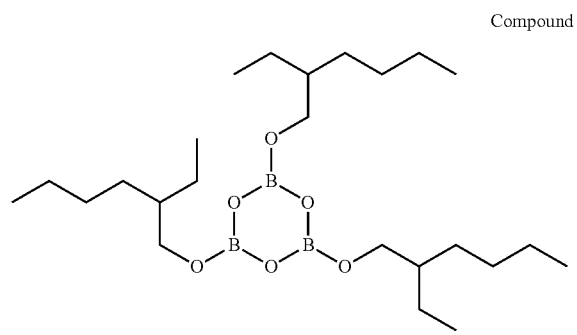
Compound A2
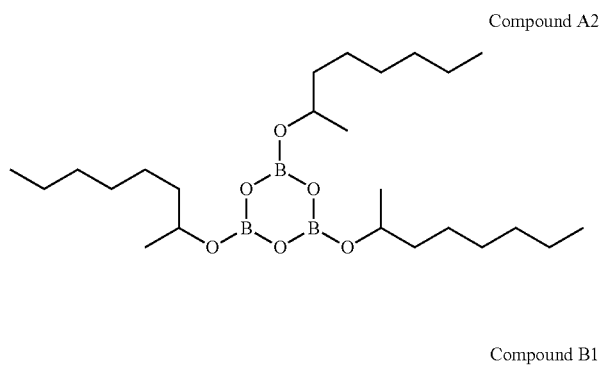
Compound B1
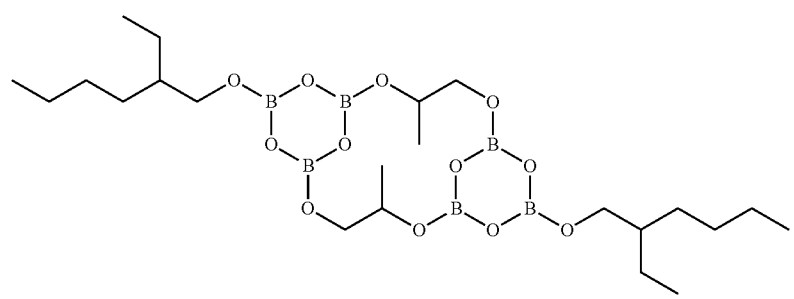
Compound B2
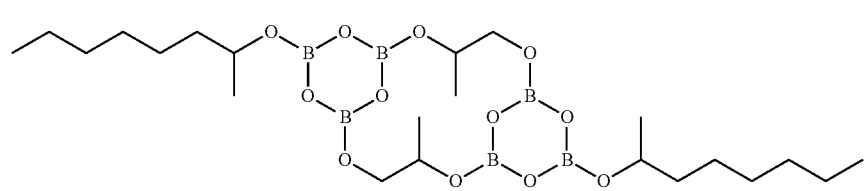
Compound B3
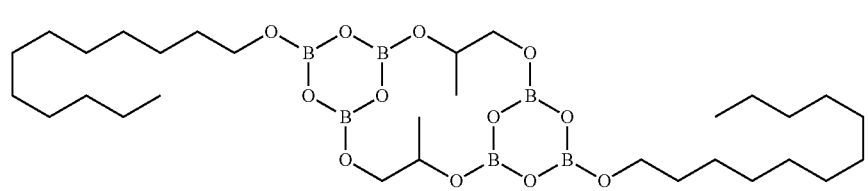
Compound B4
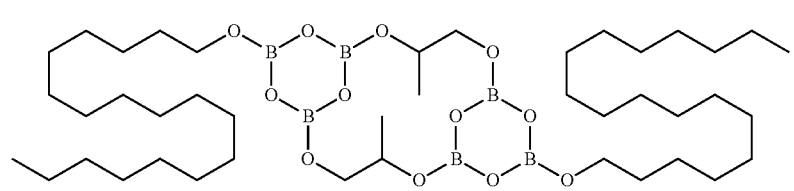
Compound C1
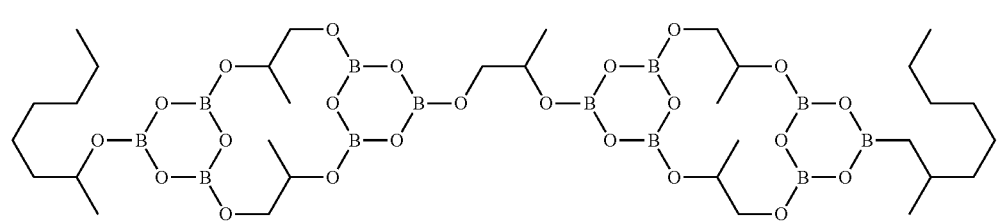
Compound C2
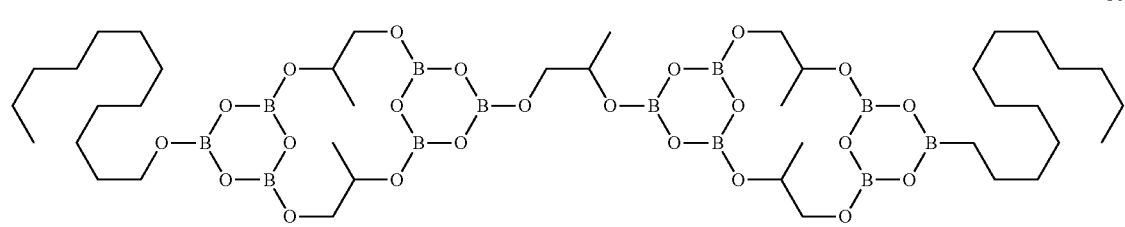

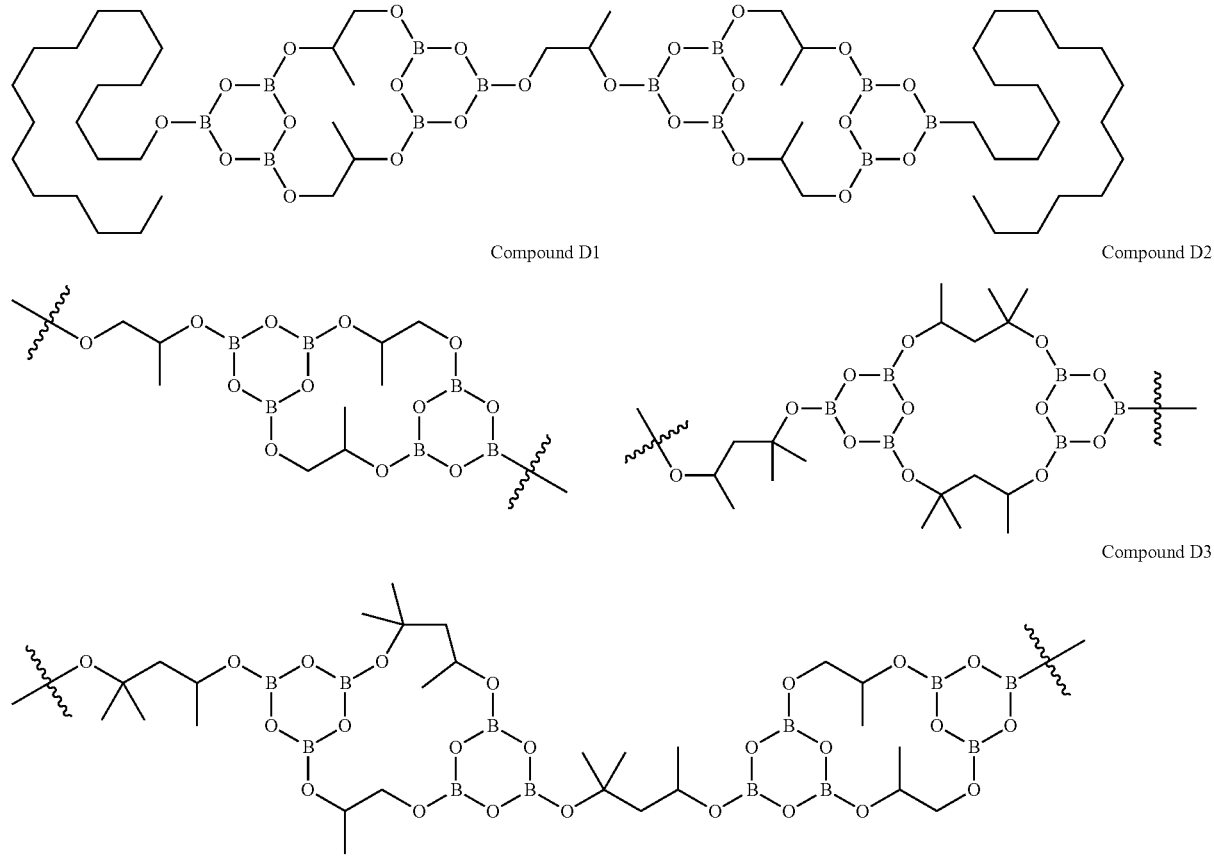

wherein the waves in Compounds D1, D2 and D3, each represent a bond between multiple Compounds D1, D2 and D3 respectively, in an oligomer or polymer form.

16. A composition comprising a compound and a diluent comprising a paraffin wax, an ester wax of vegetal or animal origin, a fatty ester, tar, a petrochemical oil, petroleum naphtha, petroleum ether, a volatile ester, and/or a volatile ether, wherein said compound is of Formula I:

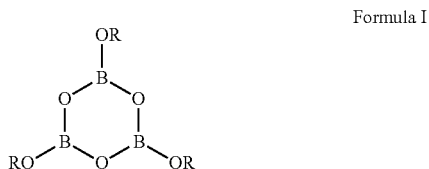

Formula I wherein
R is, independently in each instance, a group A or a primary or secondary, linear or branched $C_{8-20}$alkyl group; and
A is a primary, secondary, or tertiary, linear or branched $C_{2-10}$alkylene group wherein the $C_{2-10}$alkylene group comprises an ethylene or propylene between the oxygen atoms attached thereto, wherein said alkylene group links at least two compounds of Formula I.

17. The composition of claim 16, wherein said diluent comprises a paraffin wax.

18. The composition of claim 16, wherein said ester wax of vegetal or animal origin is selected from beeswax and carnauba wax; said fatty ester is selected from vegetable or animal oils and greases, and biodiesel; said volatile ester is selected from ethyl acetate and isopropyl acetate; or said volatile ether is selected from diethyl ether and MTBE.

19. The composition of claim 16, wherein said compound is of Formula II:

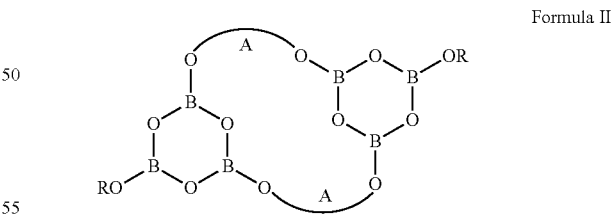

Formula II wherein,
A is, independently in each instance, selected from primary, secondary, or tertiary, linear or branched $C_{2-10}$alkylene group wherein the $C_{2-10}$alkylene group comprises an ethylene or propylene between the oxygen atoms attached thereto; and
R is as defined in claim 16.

20. The composition of claim 16, wherein said compound is of Formula III:

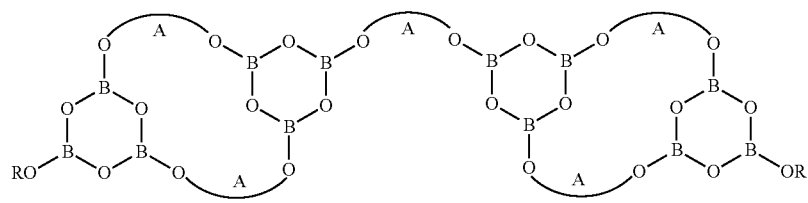

Formula III wherein A and R are as defined in claim 19.

21. The composition of claim 16, wherein said compound is of Formula IV:

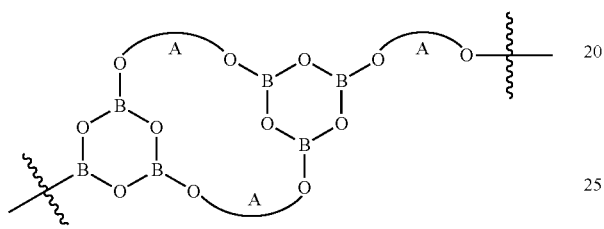

Formula IV wherein A is, independently in each instance, as defined in claim 19, and wherein the waves each represent a bond between multiple units of Formula IV in an oligomer or polymer form.

22. The composition of claim 16, wherein said compound is selected from:

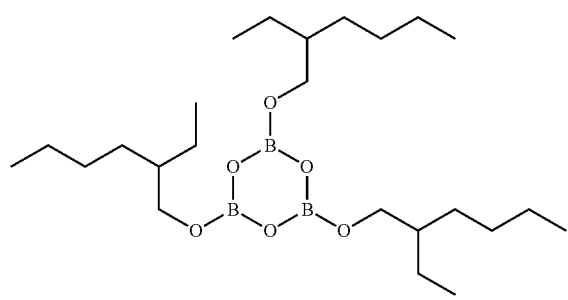

Compound A1

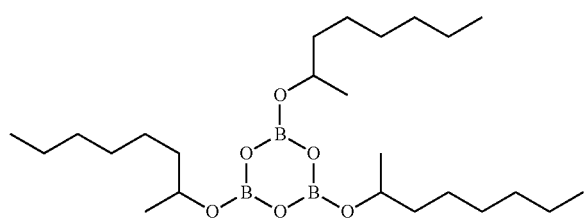

Compound A2

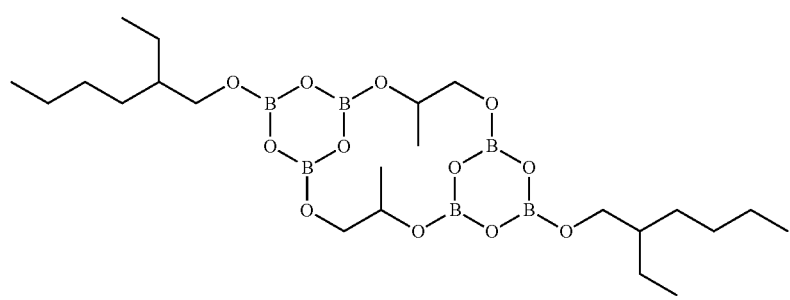

Compound B1

-continued
Compound B2
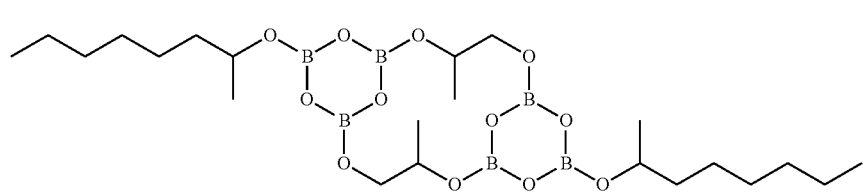
Compound B3
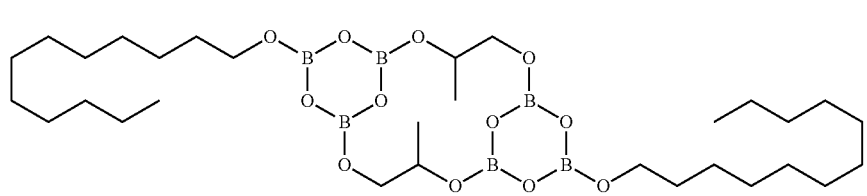
Compound B4
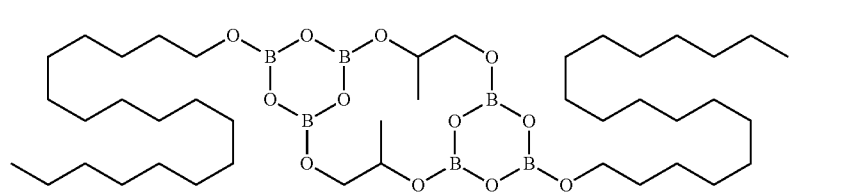
Compound C1
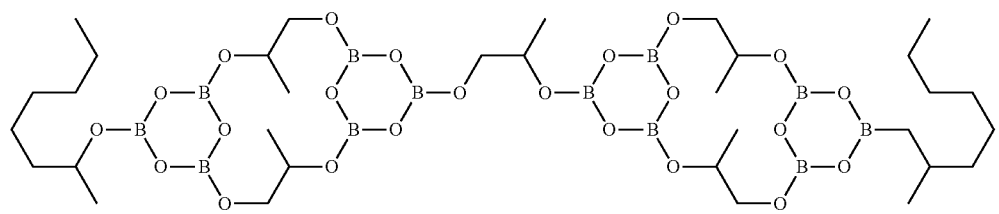
Compound C2
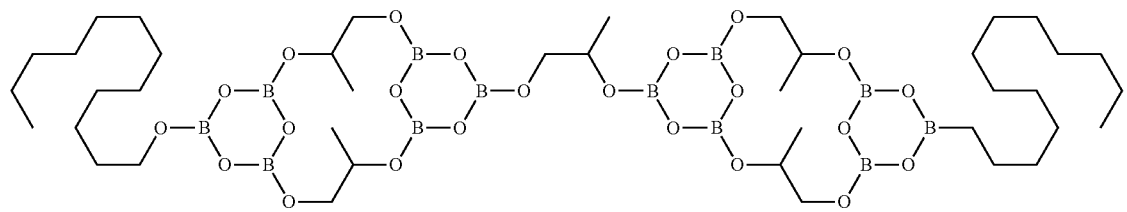
Compound C3
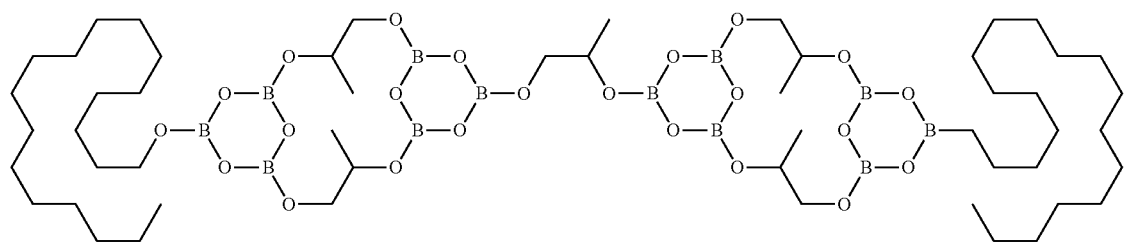
Compound D1
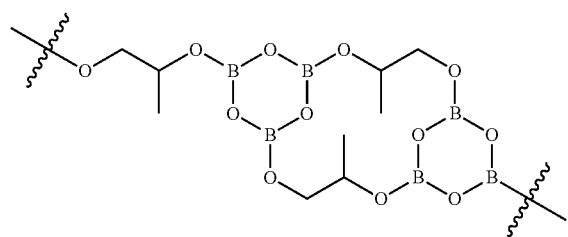
Compound D2
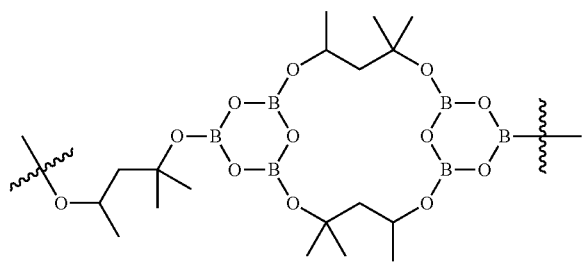

-continued

Compound D3

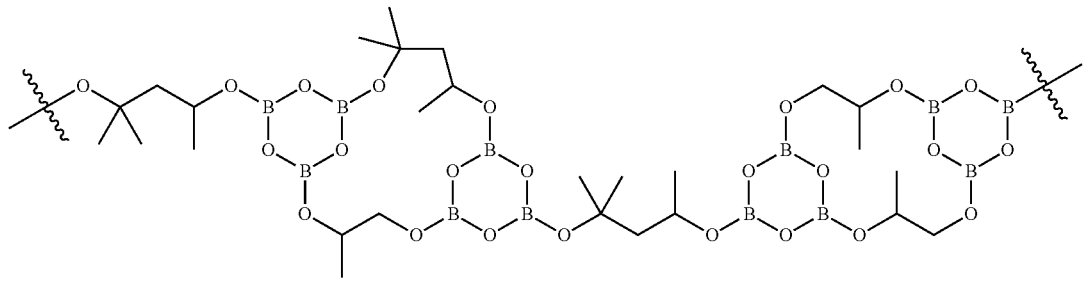

wherein the waves in Compounds D1, D2 and D3, each represent a bond between multiple Compounds D1, D2 and D3 respectively, in an oligomer or polymer form.

23. A method for protecting wood, said method comprising a step of applying on a wood surface at least one compound, or a composition comprising the at least one compound and a diluent, wherein the compound is of Formula I:

Formula I

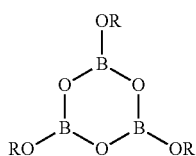

wherein

R is, independently in each instance, a group A or a primary or secondary, linear or branched $C_{8-20}$alkyl group; and A is a primary, secondary, or tertiary, linear or branched $C_{2-10}$alkylene group wherein the $C_{2-10}$alkylene group comprises an ethylene or propylene between the oxygen atoms attached thereto, wherein said alkylene group links at least two compounds of Formula I.

24. The method of claim 23, wherein the step of applying comprises impregnating said wood with said compound or composition.

25. The method of claim 23, further comprising a step of heating the compound or composition before applying.

26. The method of claim 23, wherein said protection comprises protecting said wood against moisture.

27. The method of claim 23, wherein said protection comprises preventing or reducing degradation caused by insects, microbes, or a combination thereof.

28. The method of claim 27, wherein said microbes are fungi.

29. The method of claim 23, wherein said compound is of Formula II:

Formula II

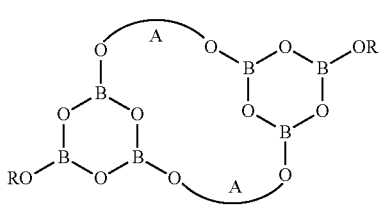

wherein,

A is, independently in each instance, selected from primary, secondary, or tertiary, linear or branched $C_{2-10}$alkylene group wherein the $C_{2-10}$alkylene group comprises an ethylene or propylene between the oxygen atoms attached thereto; and R is as defined in claim 23.

30. The method of claim 23, wherein said compound is of Formula III:

Formula III

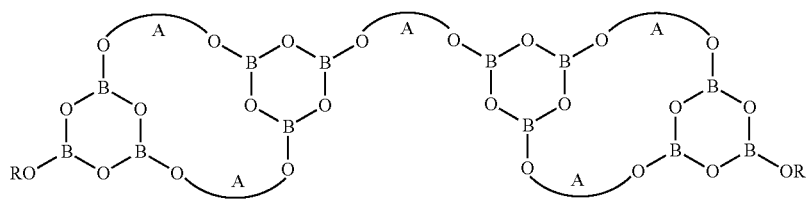

wherein A and R are as defined in claim 29.

31. The method of claim 23, wherein said compound is of Formula IV:

Formula IV

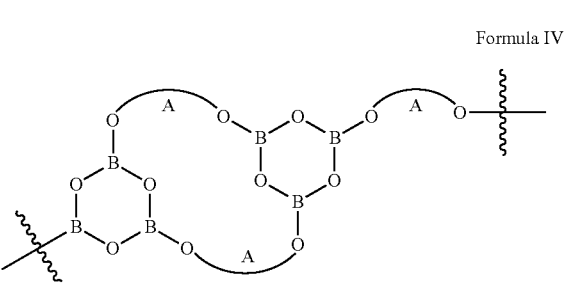

wherein A is, independently in each instance, as defined in claim 29, and wherein the waves each represent a bond between multiple units of Formula IV in an oligomer or polymer form.
32. The method of claim 23, wherein said compound is selected from:
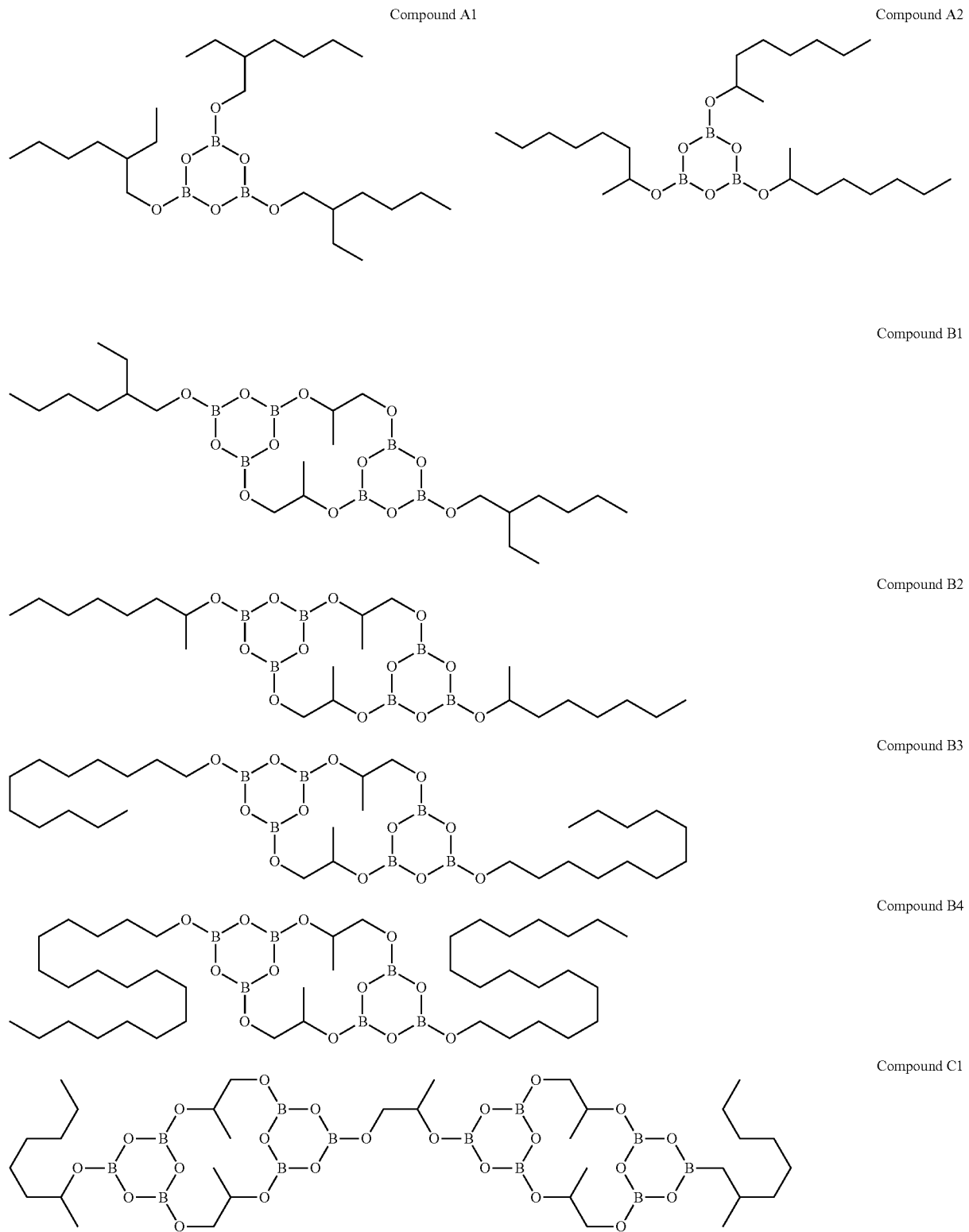

Compound C2
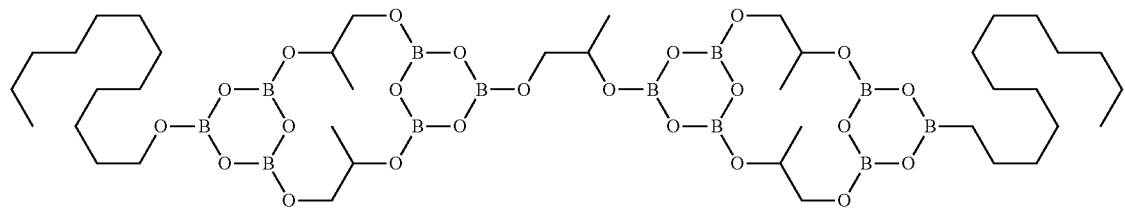
Compound C3
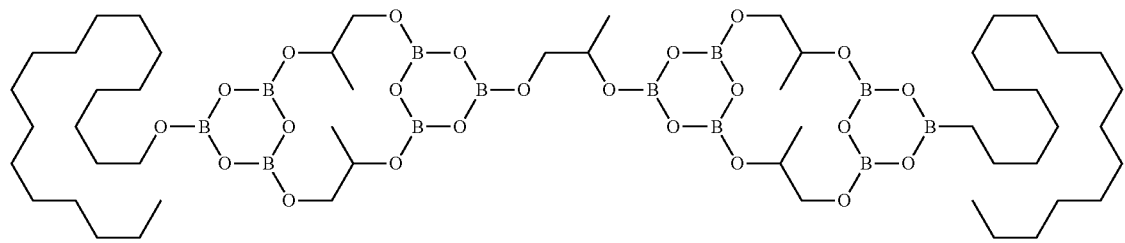
Compound D1
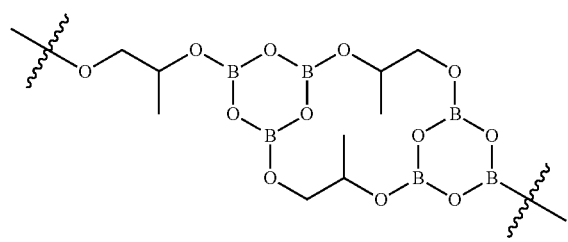
Compound D2
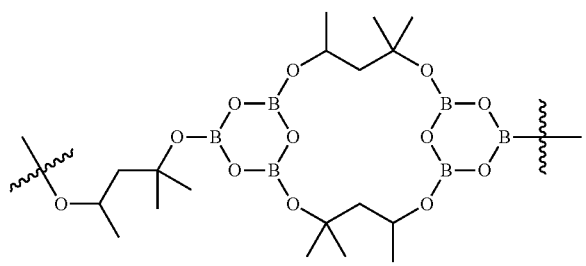
Compound D3
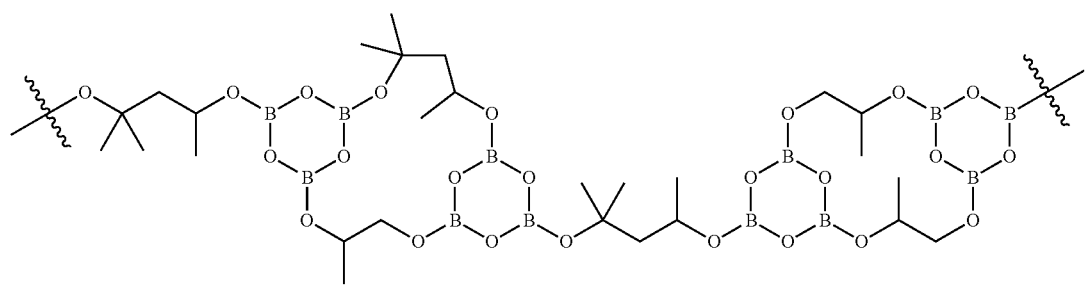
wherein the waves in Compounds D1, D2 and D3, each represent a bond between multiple Compounds D1, D2 and D3 respectively, in an oligomer or polymer form.
* * * * *